(12) United States Patent
Wang et al.

(10) Patent No.: US 9,763,575 B2
(45) Date of Patent: Sep. 19, 2017

(54) METHOD AND DEVICE FOR PROCESSING WIRELESS BODY AREA NETWORK DATA

(71) Applicant: ZTE CORPORATION, Shenzhen, Guangdong Province (CN)

(72) Inventors: Qian Wang, Shenzhen (CN); Yang Guo, Shenzhen (CN); Zhong Yu, Shenzhen (CN); Zhou Zhi, Shenzhen (CN)

(73) Assignee: ZTE CORPORATION (CN)

( * ) Notice: Subject to any disclaimer, the term of this patent is extended or adjusted under 35 U.S.C. 154(b) by 0 days.

(21) Appl. No.: 15/100,726

(22) PCT Filed: May 15, 2014

(86) PCT No.: PCT/CN2014/077558
§ 371 (c)(1),
(2) Date: Jun. 1, 2016

(87) PCT Pub. No.: WO2014/183653
PCT Pub. Date: Nov. 20, 2014

(65) Prior Publication Data
US 2016/0296115 A1 Oct. 13, 2016

(30) Foreign Application Priority Data
Dec. 5, 2013 (CN) .......................... 2013 1 0652457

(51) Int. Cl.
*G08C 19/22* (2006.01)
*A61B 5/00* (2006.01)
(Continued)

(52) U.S. Cl.
CPC ........ *A61B 5/0024* (2013.01); *G06F 19/3406* (2013.01); *H04B 13/005* (2013.01)

(58) Field of Classification Search
CPC .................................................. A61B 5/0024
(Continued)

(56) References Cited

U.S. PATENT DOCUMENTS

2004/0113771 A1   6/2004   Ozaki et al.
2008/0001735 A1*  1/2008   Tran .................... G06F 19/3418
                                              340/539.22
(Continued)

FOREIGN PATENT DOCUMENTS

CN    102123515 A    7/2011
CN    102958062 A    3/2013
(Continued)

OTHER PUBLICATIONS

International Search Report issued Sep. 1, 2014 in PCT Patent Application No. PCT/CN2014/077558.
(Continued)

*Primary Examiner* — Santiago Garcia
(74) *Attorney, Agent, or Firm* — Plumsea Law Group, LLC (57) ABSTRACT

A method and a device for processing wireless body area network data, the method is applied to a processing device for wireless body area network data and comprises: receiving or generating sampled value reference ranges; receiving sampled data from an acquisition device of wireless body area network data, and judging a sampled value reference range to which the sampled data belong according to a sampled value of the sampled data; and processing the sampled data according to the sampled value reference range to which the sampled data belong. Through the embodiments of the present document, degrees of importance of the sampled data can be automatically differentiated and the data processing efficiency is improved under the situation of limited resources.

8 Claims, 3 Drawing Sheets

(51) Int. Cl.
  *G06F 19/00* (2011.01)
  *H04B 13/00* (2006.01)
(58) Field of Classification Search
  USPC .................................................. 340/870.07
  See application file for complete search history.

(56) References Cited

U.S. PATENT DOCUMENTS

| | | | | |
|---|---|---|---|---|
| 2008/0164979 | A1* | 7/2008 | Otto ..................... | A61B 5/0002 340/286.01 |
| 2010/0027704 | A1* | 2/2010 | Ho ........................ | H04L 1/0041 375/267 |
| 2012/0224611 | A1* | 9/2012 | Baheti .................... | H03M 7/30 375/219 |
| 2014/0226837 | A1* | 8/2014 | Grokop .............. | H04M 1/6016 381/103 |
| 2014/0247206 | A1* | 9/2014 | Grokop ................ | G06F 1/3287 345/156 |
| 2014/0358473 | A1* | 12/2014 | Goel .................... | A61B 5/1118 702/141 |
| 2015/0057964 | A1* | 2/2015 | Albinali ................. | G01P 13/00 702/141 |
| 2015/0057967 | A1* | 2/2015 | Albinali ................ | A61B 5/681 702/150 |
| 2015/0205931 | A1* | 7/2015 | Wang ..................... | A61B 5/746 702/19 |

FOREIGN PATENT DOCUMENTS

| | | |
|---|---|---|
| CN | 103354652 A | 10/2013 |
| WO | 2012176193 A1 | 12/2012 |
| WO | 2014183653 A1 | 11/2014 |

OTHER PUBLICATIONS

Written Opinion issued Sep. 1, 2014 in PCT Patent Application No. PCT/CN2014/077558.
European Search Report dated Aug. 25, 2016, for EP Application No. 14798054.4.

* cited by examiner

METHOD AND DEVICE FOR PROCESSING WIRELESS BODY AREA NETWORK DATA

CROSS-REFERENCE TO RELATED APPLICATION(S)

This application is the U.S. National Phase application of PCT application number PCT/CN2014/077558 having a PCT filing date of May 15, 2014, which claims priority of Chinese patent application 2013106524576, filed on Dec. 5, 2013, the disclosures of which are hereby incorporated by reference.

TECHNICAL FIELD

The present document relates to the wireless communication field, in particular to a method and a device for processing wireless body area network data.

BACKGROUND OF THE RELATED ART

A WBAN (Wireless Body Area Network) is a communication network which is centered on a human body, is used for the purpose of acquiring various physiological parameters of the human body and consists of sensors (nodes) distributed on the surface of the human body or implanted in the human body and a personal data acquisition and processing terminal (hub node), and can realize short-distance, low-power-consumption, high-reliability and high-biosafety bidirectional data transmission under four scenarios, i.e., an in-vivo to in-vivo scenario, an to body-surface scenario, a body-surface to body-surface scenario and a body-surface to in-vitro scenario. A data transmission process of the wireless body area network comprises that the nodes acquire human body data information, package the human body data information into a frame, transmit the frame to the hub node, and the hub node processes and analyzes the frame, and completes subsequent control instruction feedback and data outward transmission functions.

Since the nodes are wearable or implanted micro-sensor devices and cannot be charged in time to supplement energy like common terminal devices, the enemy consumption problem of the nodes must be considered in a communication process of the nodes of the wireless body area network. Related wireless body area network communication methods rarely have suitable energy control strategies. In addition, although some related standards divide the priority of the communication service of the nodes, specific control methods for node transmission periods are not clearly stated.

SUMMARY

The technical problem to be solved by the present document is to provide a method and a device for processing wireless body area network data, so as to automatically differentiate the degrees of importance of sampled data and improve the data processing efficiency under the situation of limited resources.

In order to solve the technical problem, the present document provides a method for processing wireless body area network data, which is applied to a processing device for wireless body area network data, and the method comprises:

receiving or generating sampled value reference ranges;
receiving sampled data from an acquisition device of wireless body area network data, and judging a sampled value reference range to which the sampled data belong according to a sampled value of the sampled data; and processing the sampled data according to the sampled value reference range to which the sampled data belong.

Preferably, the method further has the following features: said processing the sampled data according to the sampled value reference range to which the sampled data belong comprises:

if the sampled value reference range to which the sampled data belong is a designated normal sampled value range and satisfies a designated condition, deleting the sampled data.

Preferably, the method further has the following features: there are a plurality of the sampled value reference ranges, and different sampled value reference ranges correspond to different coding accuracies; and said processing the sampled data according to the sampled value reference range to which the sampled data belong comprises:

encoding the sampled data according to a coding accuracy corresponding to the sampled value reference range to which the sampled data belong.

Preferably, the method further has the following features: after said encoding the sampled data according to a coding accuracy corresponding to the sampled value reference range to which the sampled data belong, the method further comprises:

recording a sampled coding value and sampling time of each sampled data, and generating a sampling log; and determining a priority of the sampling log according to coding accuracy information of a sampled data coding value and sampling time information in the sampling log; if the priority is greater than a first priority threshold, notifying the acquisition device to shorten a data sampling period; and if the priority is smaller than or equal to the first priority threshold, notifying the acquisition device to prolong the sampling period or maintain the sampling period unchanged.

Preferably, the method further has the following features: after said determining a priority of the sampling log according to coding accuracy information of a sampled data coding value and the sampling time information in the sampling log, the method further comprises:

if the priority is greater than a second priority threshold, shortening a data transmission period; and if the priority is smaller than or equal to the second priority threshold, prolonging the transmission period or maintaining the transmission period unchanged.

Preferably, the method further has the following features: said determining a priority P of the sampling log is implemented through the following way:

$$p = \begin{cases} 0, & \text{A sampling long only contains a coding value with a lowest coding accuracy,} \\ \dfrac{\sum_{j=0}^{N-1} T_j}{T_{log}}, & \text{others} \\ 1, & \text{A sampling log contains a coding value with a highest coding accuracy.} \end{cases}$$

wherein, $$T_j = \begin{cases} 0 & \text{A coding value at time } tj \text{ is a coding value with a lowest coding accuracy.} \\ t_{j+1} - t_j & j \neq N \\ t_{cur} - t_j & j = N \end{cases}$$

$T_{log} = t_{cur} - t_{first}$, $T_{log}$ is a duration of the sampling log, $t_{cur}$ is a current time and $t_{first}$ is a first sampling time of the sampling log;

$T_j$ is a duration of a $(j+1)^{th}$ coding value in the sampling log, wherein $t_j$ is a sampling time of a $(j+1)^{th}$ coding value in the sampling log, denotes an item number in the sampling log and N denotes a total number of items contained in the sampling log.

In order to solve the problem, the present document further provides a processing device for wireless body area network data, which comprises:

a first module configured to receive or generate sampled value reference ranges;

a second module configured to receive sampled data from an acquisition device of wireless body area network data, and judge a sampled value reference range to which the sampled data belong according to a sampled value of the sampled data; and a third module configured to process the sampled data according to the sampled value reference range to which the sampled data belong.

Preferably, the device further has the following features:

the third module is configured as that processing the sampled data according to the sampled value reference range to which the sampled data belong comprises: if the sampled value reference range to which the sampled data belong is a designated normal sampled value range and satisfies a designated condition, deleting the sampled data.

Preferably, the device further has the following features:

the first module is configured as that there are a plurality of sampled value reference ranges received or generated, different sampled value reference ranges correspond to different coding accuracies; and the third module is configured as that processing the sampled data according to the sampled value reference range to which the sampled data belong comprises: encoding the sampled data according to a coding accuracy corresponding to the sampled value reference range to which the sampled data belong.

Preferably, the device further has the following features:

the third module is configured to, after encoding the sampled data according to a coding accuracy corresponding to the sampled value reference range to which the sampled data belong, further record a sampled coding value and sampling time of each sampled data, and generate a sampling log; determine a priority of the sampling log according to coding accuracy information of a sampled data coding value and sampling time information in the sampling log; if the priority is greater than a first priority threshold, notify the acquisition device to shorten a data sampling period; and if the priority is smaller than or equal to the first priority threshold, notify the acquisition device to prolong the sampling period or maintain the sampling period unchanged.

Preferably, the device further has the following features:

the third module is configured to, after determining the priority of the sampling log according to coding accuracy information of a sampled data coding value and the sampling time information in the sampling log, further, if the priority is greater than a second priority threshold, shorten a data transmission period; and if the priority is smaller than or equal to the second priority threshold, prolong the transmission period or maintain the transmission period unchanged.

Preferably, the device further has the following features:

the third module is configured to determine a priority P of the sampling log through the following way:

$$p = \begin{cases} 0, & \text{A sampling log only contains a coding value with a lowest coding accuracy.} \\ \dfrac{\sum_{j=0}^{N-1} T_j}{T_{log}}, & \text{others} \\ 1, & \text{A sampling log contains a coding value with a highest coding accuracy.} \end{cases}$$

wherein, $$T_j = \begin{cases} 0 & \text{A coding value at time } tj \text{ is a coding value with a lowest coding accuracy.} \\ t_{j+1} - t_j & j \neq N \\ t_{cur} - t_j & j = N \end{cases}$$

$T_{log} = t_{cur} - t_{first}$, $T_{log}$ is a duration of the sampling log, $t_{cur}$ is a current time and $t_{first}$ is a first sampling time of the sampling log;

$T_j$ is a duration of a $(j+1)^{th}$ coding value in the sampling log, wherein $t_j$ is a sampling time of a $(j+1)^{th}$ coding value in the sampling log, j+1 denotes an item number in the sampling log and N denotes a total number of items contained in the sampling log.

To sum up, the method and the device for processing wireless body area network data provided by the embodiments of the present document can automatically differentiate degrees of importance of the sampled data and improve the data processing efficiency under the situation of limited resources.

PREFERRED EMBODIMENTS

The embodiments of the present document will be described below in detail in combination with the drawings. It needs to be stated that the embodiments in the present application and the features in the embodiments can be freely combined under the situation of no conflict.

Figure 1:
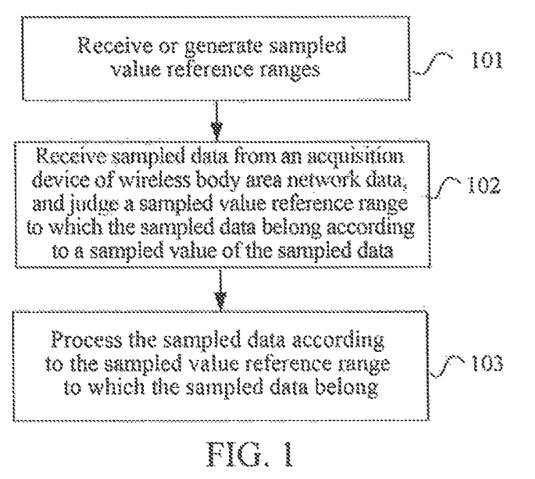
FIG. 1 is a flowchart of a method for processing wireless body area network data according to the embodiment of the present document.
Figure 2:
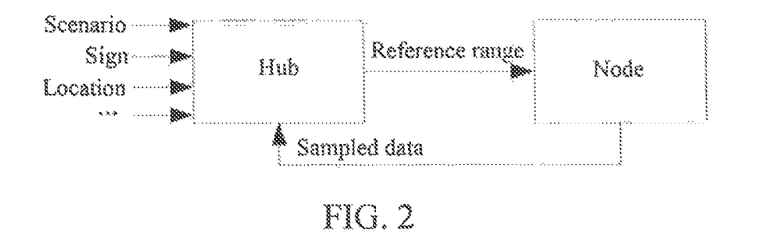
FIG. 2 is a schematic diagram of acquisition of a sampled value reference range according to the embodiment of the present document.
Figure 3:
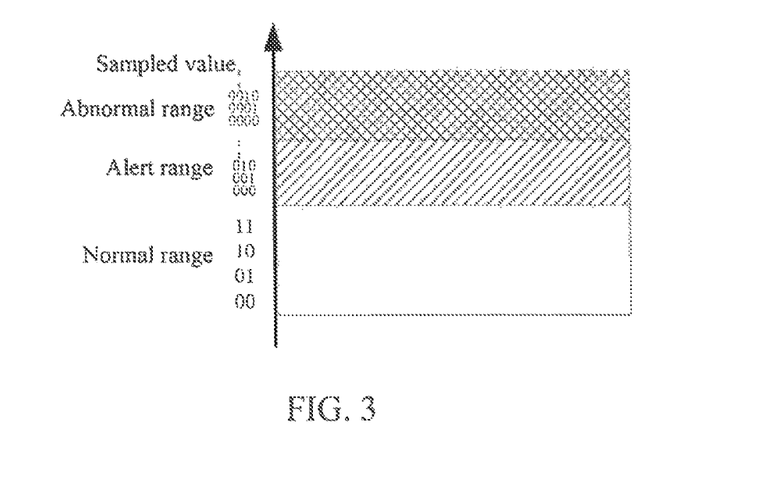
FIG. 3 is a schematic diagram of a sampled value reference range according to the embodiment of the present document.

FIG. 1 is a flowchart of a method for processing wireless body area network data according to the embodiment of the present document. The method may comprise:

In step 101, sampled value reference ranges are received or generated;

A hub node calculates to obtain a sampled value reference range of a node according to external input (scenario entry, human body sign entry, geographical environment entry, etc.) and/or internal input (node sampled value feedback); and this range may indicate a degree of importance of sampled data, and a possible form of reference range comprises a normal range, an alert range and an abnormal range, as shown in FIG. 3. The hub node transmits the reference range to the node, as shown in FIG. 2.

In addition, the node itself may generate the sampled value reference range according to external input (scenario entry, human body sign entry, geographical environment entry, etc.) and/or internal input (node sampled value feedback) under the support of certain functions, and the sampled value reference range does not need to be transmitted by the hub node to the node.

In step 102, sampled data are received from an acquisition device of wireless body area network data, and a sampled value reference range to which the sampled data belong is judged according to a sampled value of the sampled data;

In step 103: the sampled data are processed according to the sampled value reference range to which the sampled data belong;

After sampling each time, the node encodes the sampled data according to the reference range, the sampled value within a low importance range is encoded with a low coding accuracy, and the sample value within a high importance range is coded with a high coding accuracy. Thus, the deuces of importance of the sampled data may be automatically differentiated and the data processing efficiency is improved under the situation of limited resources.

In this embodiment, with respect to data with lower importance, the data are encoded with shorter bits and transmission overhead can be reduced; and with respect to data with higher importance, the data are encoded with longer bits to guarantee data accuracy and thus the data transmission efficiency can be improved.

For example, as shown in FIG. 3, the sampled value in the normal range is encoded with two bits, the sampled value in the alert range is encoded with three bits, and the sampled value in the abnormal range is encoded with four bits.

Figure 4:
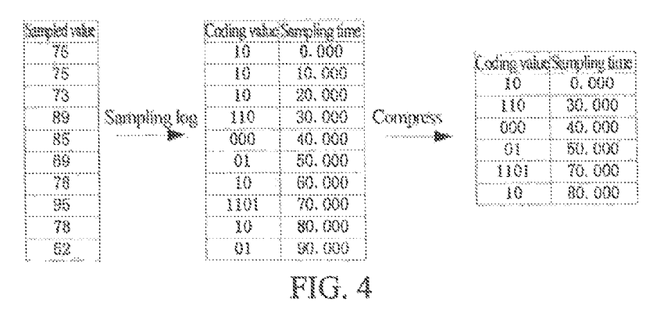
FIG. 4 is an exemplary diagram of a generated sampling log according to the embodiment of the present document.

In this embodiment, the sampled value and sampling time may be sequentially recorded to generate a sampling log. Since the sampling period of the sensor may be very short, sampled data of more than one times may be generated a data set, then the data set is transmitted and thus the transmission overhead may be reduced. During this period, the data set may also be modified, e.g., the data in the data set are cut, and thus the transmission overhead may be further reduced. For example, if the sampled data belong to the normal range, the sampled data may be deleted; or if it is judged that the sampled data belong to the normal range, one of the sampled data which belong to the normal range may be reserved and one may be deleted; and a plurality of sampled data may also be reserved and then a plurality of sampled data which belong to the normal range may be continuously deleted, etc.

The node may further cut items in the generated sampling log. A possible way is to properly delete the sampled values with low coding accuracy and reserve the sampled values with high coding accuracy. Cutting for the sampling log may be performed at a proper time as required, e.g., at any time before a transmission time point.

FIG. 4 is an exemplary diagram of a generated sampling log according to the embodiment of the present document. Low-bit sampled values which appear continuously are merged (part of two-bit data items are deleted), high-bit sampled values are reserved and the data transmission amount is compressed. For example, when the node transmits human body heart rate values to the hub node, the heart rate values in the normal range may be encoded with code elements with lower coding accuracy, and some sampled values in the normal range may also be properly deleted; and the abnormal values are encoded with higher coding accuracy, and these abnormal values may also be reserved for waiting for transmission.

In this embodiment, the data sampling period and the transmission period may also be adjusted. Supposing that the data transmission period is T and the data sampling period is t, adjusting ways for T and t are as follows:

Within the transmission T, a Node calculates a priority P of the sampled log and adjusts sampled period t according to a property item of the sampled value (e.g., coding accuracy and sampled time of a sampled value) contained in a sampled log. When the P is higher than an adjustment threshold of the sampled period t, t is shortened, and contrarily, t is maintained unchanged or prolonged.

When the priority is higher than a threshold, it indicates that the data set (i.e., the sampling log) obtained through sampling has higher transmission necessity and urgency, thus the sampling period should be shortened to obtain more timely data sources; and contrarily, if the priority is lower than the threshold, it indicates that the data set obtained through sampling is not so important that the current sampling period may be maintained unchanged or prolonged to achieve the purpose of reducing the overhead.

Figure 6:
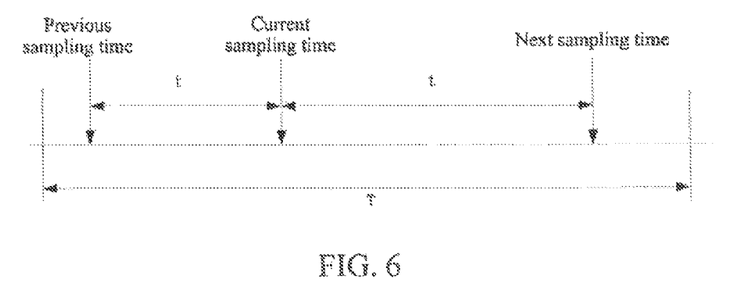
FIG. 6 is a schematic diagram of adjustment of a sampling period t according to the embodiment of the present document.

In this embodiment, the adjustment implementation way of the sampling period t is as follow: a next sampling time may be changed within the current transmission period T according to a relationship between the current sampling log priority and the sampling period t adjustment threshold, e.g., an incoming time of the next sampling time may be shortened if the current sampling log priority is greater than the sampling period t adjustment threshold, and contrarily, the incoming time of the next sampling time is prolonged, as shown FIG. 6. In order to reduce the calculation overhead, the adjustment strategy of the sampling period t is uncertainly executed after each time of sampling and within each transmission period.

Before the arrival of the transmission time, the node adjusts the transmission period T according to the calculated priority P of the sampling log in the current time: when the P is higher than the transmission period T adjustment threshold, T is shortened, and contrarily, T is maintained unchanged or is prolonged.

When the priority is higher than the threshold, it indicates that the data set (i.e. the sampling log) obtained through sampling has higher transmission necessity and urgency, thus the transmission period should be shortened to enable the hub node to obtain timely data sources; and contrarily, when the priority is lower than the threshold, it indicates that the data set obtained through sampling is not so important that the current transmission period may be maintained unchanged or prolonged to achieve the purpose of reducing the overhead (since overheads will be caused to the node and the hub node when the node transmits the sampling log to the hub node each time, and the more frequent the transmission is, the greater the overhead is and the more the consumed resources are).

Figure 5A:
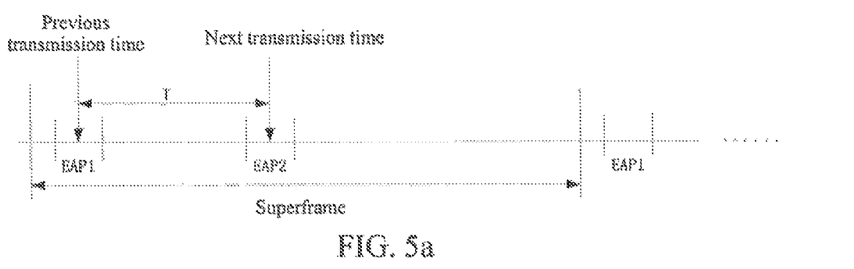
FIG. 5a and FIG. 5b are schematic diagrams of adjustment of a transmission period T according to the embodiment of the present document.
Figure 5B:
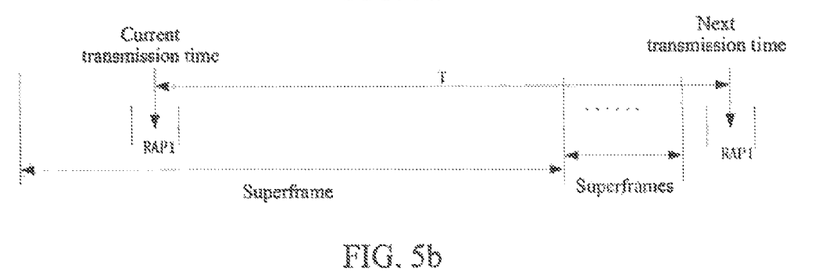

As shown in FIG. 4, since one code element with the highest coding accuracy exists, the priority thereof is equal to 1. Supposing that adjustment threshold of the transmission period T is 0.5, the transmission period T should be shortened. A possible implementation way is to access to media when the closest next access opportunity comes. For example, when the closest EAP (Exclusive Access Period) in 802.15.6 comes, the data frame consisting of the sampling log is immediately transmitted to the hub node, as shown in FIG. 5a; and if only code element with the lowest coding accuracy exists in the sampling log, all of the sampled values are within the normal range, the sampling log priority is equal to 0, if the adjustment threshold of the transmission period T is unchanged, the transmission period T should be prolonged, and in this embodiment, the subsequent access opportunity may be abandoned and continuously to wait. For example, when a next RAP (Random Access Period) or CAP (Contention Access Period) in 802.15.6 comes, the node having the sampling log does not join in the random contention process, as shown in FIG. 5b; and in addition, if the priority of the sampling log is between 0 and 1, the access opportunity should be properly selected according to the relationship between the priority and the transmission period T adjustment threshold, so as to adjust the transmission period T.

When the transmission time arrives, the node packages the sampling log into the data frame and calibrates the priority of the frame according to the priority of the sampling log, wherein the priority of the frame is in direct proportion to P. Thereafter, the node transmits the data frame to the hub node.

In this embodiment, the calculation way of the sampling log priority P is as follow:

if the sampling log only contains a coding value with the lowest coding accuracy, P=0 (lowest);

if the sampling log contains a coding value with the highest coding accuracy, P=1 (highest);

and under other situations, $$P = \frac{\sum_{j=0}^{N-1} T_j}{T_{log}},$$

wherein, $$T_j = \begin{cases} 0 & \text{A coding value at time } tj \text{ is a coding value with a lowest coding accuracy.} \\ t_{j+1} - t_j & j \neq N \\ t_{cur} - t_j & j = N \end{cases}$$

$T_{log}$ is a duration of the sampling log and the calculation way is: $T_{log}=t_{cur}-T_{first}$, wherein $t_{cur}$ is a current time and is the first sampling time of the sampling log.

$T_j$ is a duration of a $(j+1)^{th}$ coding value in the sampling log, wherein $t_j$ is a sampling time of a $(j+1)^{th}$ coding value in the sampling log, j+1 denotes an item number in the sampling log and N denotes the total number of items contained in the sampling log.

The sampling period t is uncertainly adjusted within each transmission period T or after sampling each time, and may be adjusted at a proper time as required; and the transmission period T is uncertainly adjusted each time and may be adjusted at a proper time as required.

Figure 7:
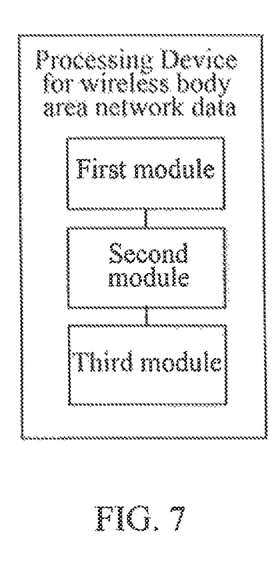
FIG. 7 is a schematic diagram of a device for processing wireless body area network data according to the embodiment of the present document.

FIG. 7 is a schematic diagram of a processing device for wireless body area network data. according to the embodiment of the present document. As shown in FIG. 7, the device provided by this embodiment may comprise:

a first module configured to receive or generate sampled value reference ranges;

a second module configured to receive sampled data from an acquisition device of wireless body area network data, and judge a sampled value reference range to which the sampled data belong according to a sampled value of the sampled data; and a third module configured to process the sampled data according to the sampled value reference range to which the sampled data belong.

In one preferred embodiment, the third module processing the sampled data according to the sampled value reference range to which the sampled data belong may comprises: if the sampled value reference range to which the sampled data belong is a designated normal sampled value range and satisfies a designated condition, the sampled data are deleted.

Herein, the designated condition satisfied by the sampled data may include but not limited to that: the sampled data belong to (even number)$^{th}$ sampled data in the normal range or a plurality of continuous sampled data, etc.

In one preferred embodiment, the first module may receive or generate a plurality of sampled value reference ranges, different sampled value reference ranges correspond to different coding accuracies; and the third module processing the sampled data according to the sampled value reference range to which the sampled data belong may comprises: the sampled data are encoded according to a coding accuracy corresponding to the sampled value reference range to which the sampled data belong.

In one preferred embodiment, after the third module encodes the sampled data according to a coding accuracy corresponding to the sampled value reference range to which the sampled data belong, it is further configured to record a sampled coding value and sampling time of each sampled data, and generate a sampling log; and determine a priority of the sampling log according to coding accuracy information of a sampled data coding value and sampling time information in the sampling log, if the priority is greater than a first priority threshold, notify the acquisition device to shorten a data sampling period; and if the priority is smaller than or equal to the first priority threshold, notify the acquisition device to prolong the sampling period or maintain the sampling period unchanged.

In one preferred embodiment, after the third module determines the priority of the sampling log according to the coding accuracy information of a sampled data coding value and the sampling time information in the sampling log, it is further configured to, if the priority is greater than a second priority threshold, shorten a data transmission period; and if the priority is smaller than or equal to the second priority threshold, prolong the transmission period or maintain the transmission period unchanged.

In one preferred embodiment, the third module determines the priority P of the sampling log through the following way:

$$p = \begin{cases} 0, & \text{A sampling log only contains a coding value with a lowest coding accuracy.} \\ \dfrac{\sum_{j=0}^{N-1} T_j}{T_{log}}, & \text{others} \\ 1, & \text{A sampling log contains a coding value with a highest coding accuracy.} \end{cases}$$

wherein, $$T_j = \begin{cases} 0 & \text{A coding value at time } tj \text{ is a coding value with a lowest coding accuracy.} \\ t_{j+1} - t_j & j \neq N \\ t_{cur} - t_j & j = N \end{cases}$$

$T_{log} = t_{cur} - t_{first}$, $T_{log}$ is a duration of the sampling log, $t_{cur}$ is a current time and $t_{first}$ is the first sampling time of the sampling log;

$T_j$ is a duration of a $(j+1)^{th}$ coding value in the sampling log, wherein $t_j$ is a sampling time of a $(j+1)^{th}$ coding value in the sampling log, j+1 denotes an item number in the sampling log and N denotes the total number of items contained in the sampling log.

One ordinary skilled in the art can understand that all or partial steps in the above-mentioned methods can be completed by relevant hardware instructed by a program, and the program can be stored in a computer readable storage medium such as a read only memory, a magnetic disk or a compact disk, etc. Optionally, all or partial steps of the above-mentioned embodiments can also be implemented by using one or more integrated circuits. Correspondingly, each module/unit in the above-mentioned embodiments can be implemented by means of hardware, and can also be implemented by means of a software function module. The present document is not limited to combinations of hardware and software in any specific form.

The embodiments are just preferred embodiments of the present document. The present document may also have other emodiments. One skilled in the art can make various corresponding modifications and variations according to the present document. However, all these corresponding modifications and variations shall also belong to the protection range of claims annexed to the present document.

INDUSTRIAL APPLICABILITY

Compared with the prior art, the embodiments of the present document have the following advantages:

1) The sampled value reference ranges can be adjusted according to conditions such as environments and signs, the degrees of importance of the sampled data can be evaluated according to the sampled value reference ranges, the sampled value coding values (i.e., coding accuracy) are configured, the degrees of importance of the sampled data can be very directly known and the data processing efficiency is improved under the situation of limited resources.

2) The data transmission amount can be compressed and the node energy consumption is reduced according to the sampled value reference ranges.

3) The data sampling period and the transmission period can be adjusted and the node energy consumption can be reduced according to the priority of the sampled value

We claim:

1. A method for processing wireless body area network data, applied to a processing device for wireless body area network data, comprising:
receiving or generating sampled value reference ranges;
receiving sampled data from an acquisition device of wireless body area network data, and judging a sampled value reference range to which the sampled data belong according to a sampled value of the sampled data; and
processing the sampled data according to the sampled value reference range to which the sampled data belong;
wherein there are a plurality of the sampled value reference ranges, and different sampled value reference ranges correspond to different coding accuracies; and
said processing the sampled data according to the sampled value reference range to which the sampled data belong comprises:
encoding the sampled data according to a coding accuracy corresponding to the sampled value reference range to which the sampled data belong;
wherein, after said encoding the sampled data according to a coding accuracy corresponding to the sampled value reference range to which the sampled data belong, the method further comprises:
recording a sampled coding value and sampling time of each sampled data, and generating a sampling log; and
determining a priority of the sampling log according to coding accuracy information of a sampled data coding value and sampling time information in the sampling log;
wherein said determining a priority P of the sampling log is implemented through the following way:

$$p = \begin{cases} 0, & \text{A sampling log only contains a coding value with a lowest coding accuracy,} \\ \dfrac{\sum_{j=0}^{N-1} T_j}{T_{log}}, & \text{Others} \\ 1, & \text{A sampling log contains a coding value with a highest coding accuracy,} \end{cases}$$

wherein $$T_j = \begin{cases} 0 & \text{A coding value at time } tj \text{ is a coding value with a lowest coding accuracy,} \\ t_{j+1} - t_j & j \neq N \\ t_{cur} - t_j & j = N \end{cases}$$

$T_{log} = t_{cur} - t_{first}$, $T_{log}$ is a duration of the sampling log, $t_{cur}$ is a current time and $t_{first}$ is a first sampling time of the sampling log;

$T_j$ is a duration of a $(j+1)^{th}$ coding value in the sampling log, wherein $t_j$ is a sampling time of a $(j+1)^{th}$ coding value in the sampling log, j+1 denotes an item number in the sampling log and N denotes a total number of items contained in the sampling log.

2. The method according to claim 1, wherein said processing the sampled data according to the sampled value reference range to which the sampled data belong comprises:
if the sampled value reference range to which the sampled data belong is a designated normal sampled value range and satisfies a designated condition, deleting the sampled data.

3. The method according to claim 1, wherein, the method further comprises:
if the priority is greater than a first priority threshold, notifying the acquisition device to shorten a data sampling period; and if the priority is smaller than or equal to the first priority threshold, notifying the acquisition device to prolong the sampling period or maintain the sampling period unchanged.

4. The method according to claim 3, wherein, after said determining a priority of the sampling log according to coding accuracy information of a sampled data coding value and the sampling time information in the sampling log, the method further comprises:
if the priority is greater than a second priority threshold, shortening a data transmission period; and if the priority is smaller than or equal to the second priority threshold, prolonging the transmission period or maintaining the transmission period unchanged.

5. A processing device for wireless body area network data, comprising hardware performing instructions stored in a non-transitory computer readable medium which executes steps in the following modules:
a first module configured to receive or generate sampled value reference ranges;
a second module configured to receive sampled data from an acquisition device of wireless body area network data, and judge a sampled value reference range to which the sampled data belong according to a sampled value of the sampled data; and
a third module configured to process the sampled data according to the sampled value reference range to which the sampled data belong;
the first module being configured such that there are a plurality of sampled value reference ranges received or generated, different sampled value reference ranges correspond to different coding accuracies; and
the third module being configured such that processing the sampled data according to the sampled value reference range to which the sampled data belong comprises: encoding the sampled data according to a coding accuracy corresponding to the sampled value reference range to which the sampled data belong;
wherein the third module is configured to, after encoding the sampled data according to a coding accuracy corresponding to the sampled value reference range to which the sampled data belong, further record a sampled coding value and sampling time of each sampled data, and generate a sampling log; determine a priority of the sampling log according to coding accuracy information of a sampled data coding value and sampling time information in the sampling log;
the third module is configured to determine a priority P of the sampling log through the following way:

$$p = \begin{cases} 0, & \text{A sampling log only contains a coding value with a lowest coding accuracy,} \\ \dfrac{\sum_{j=0}^{N-1} T_j}{T_{log}}, & \text{Others} \\ 1, & \text{A sampling log contains a coding value with a highest coding accuracy,} \end{cases}$$

wherein, $$T_j = \begin{cases} 0 & \text{A coding value at time } tj \text{ is a coding value with a lowest coding accuracy,} \\ t_{j+1} - t_j & j \neq N \\ t_{cur} - t_j & j = N \end{cases}$$

$T_{log} = t_{cur} - t_{first}$, $T_{log}$ is a duration of the sampling log, $t_{cur}$ is a current time and $t_{first}$ is a first sampling time of the sampling log;
$T_j$ is a duration of a $(j+1)^{th}$ coding value in the sampling log, wherein $t_j$ is a sampling time of a $(j+1)^{th}$ coding value in the sampling log, j+1 denotes an item number in the sampling log and N denotes a total number of items contained in the sampling log.

6. The device according to claim 5, wherein,
the third module is configured such that processing the sampled data according to the sampled value reference range to which the sampled data belong comprises: if the sampled value reference range to which the sampled data belong is a designated normal sampled value range and satisfies a designated condition, deleting the sampled data.

7. The device according to claim 5, wherein,
the third module is configured to, if the priority is greater than a first priority threshold, notify the acquisition device to shorten a data sampling period, and if the priority is smaller than or equal to the first priority threshold, notify the acquisition device to prolong the sampling period or maintain the sampling period unchanged.

8. The device according to claim 7, wherein,
the third module is configured to, after determining a priority of the sampling log according to coding accuracy information of a sampled data coding value and the sampling time information in the sampling log, further, if the priority is greater than a second priority threshold, shorten a data transmission period; and if the priority is smaller than or equal to the second priority threshold, prolong the transmission period or maintain the transmission period unchanged.

* * * * *